(12) United States Patent
Xu

(10) Patent No.: US 12,414,914 B2
(45) Date of Patent: Sep. 16, 2025

(54) DOCETAXEL COMPOSITION FOR INJECTION AND PREPARATION METHOD THEREFOR

(71) Applicant: BIKA BIOTECHNOLOGY (GUANGZHOU) CO., LTD, Guangzhou (CN)

(72) Inventor: Yingting Xu, Guangzhou (CN)

(73) Assignee: BIKA BIOTECHNOLOGY (GUANGZHOU) CO., LTD, Guangzhou (CN)

( * ) Notice: Subject to any disclaimer, the term of this patent is extended or adjusted under 35 U.S.C. 154(b) by 356 days.

(21) Appl. No.: 17/262,608

(22) PCT Filed: Aug. 2, 2018

(86) PCT No.: PCT/CN2018/098227
§ 371 (c)(1),
(2) Date: May 19, 2021

(87) PCT Pub. No.: WO2020/019363
PCT Pub. Date: Jan. 30, 2020

(65) Prior Publication Data
US 2021/0393514 A1 Dec. 23, 2021

(30) Foreign Application Priority Data
Jul. 25, 2018 (CN) .......................... 201810838844.1

(51) Int. Cl.
| A61K 9/00 | (2006.01) |
|---|---|
| A61K 9/08 | (2006.01) |
| A61K 9/19 | (2006.01) |
| A61K 31/337 | (2006.01) |
| A61K 47/10 | (2017.01) |
| A61K 47/12 | (2006.01) |
| A61K 47/32 | (2006.01) |
| A61K 47/40 | (2006.01) |

(52) U.S. Cl.
CPC .............. *A61K 9/0019* (2013.01); *A61K 9/08* (2013.01); *A61K 9/19* (2013.01); *A61K 31/337* (2013.01); *A61K 47/10* (2013.01); *A61K 47/12* (2013.01); *A61K 47/32* (2013.01); *A61K 47/40* (2013.01)

(58) Field of Classification Search
None
See application file for complete search history.

(56) References Cited

U.S. PATENT DOCUMENTS

| 6,284,746 | B1 | 9/2001 | Szente et al. | |
|---|---|---|---|---|
| 8,044,093 | B2 * | 10/2011 | Hao | A61P 35/04 |
| | | | | 514/449 |
| 8,481,511 | B2 * | 7/2013 | Ren | A61K 31/337 |
| | | | | 514/449 |
| 8,765,716 | B2 | 7/2014 | Ren et al. | |
| 8,791,152 | B2 * | 7/2014 | Kim | A61K 47/10 |
| | | | | 514/449 |
| 2003/0044356 | A1 | 3/2003 | Auh et al. | |
| 2005/0009783 | A1 | 1/2005 | Kagkadis | |
| 2005/0069590 | A1 | 3/2005 | Buehler et al. | |
| 2006/0153867 | A1 * | 7/2006 | Li | A61K 38/08 |
| | | | | 514/23 |
| 2009/0163574 | A1 * | 6/2009 | Kim | A61K 47/10 |
| | | | | 514/449 |
| 2011/0105598 | A1 | 5/2011 | Gurjar et al. | |
| 2015/0328321 | A1 * | 11/2015 | Alakhov | A61K 9/19 |
| | | | | 514/449 |
| 2020/0268705 | A1 | 8/2020 | Tong et al. | |

FOREIGN PATENT DOCUMENTS

| CN | 1222321 C | 10/2005 |
|---|---|---|
| CN | 100411688 C | 8/2008 |
| CN | 101439017 A | 5/2009 |
| CN | 101484137 A | 7/2009 |
| CN | 101868227 A | 10/2010 |
| CN | 102793678 * | 11/2012 |
| CN | 105142671 A | 12/2015 |
| CN | 108066774 * | 5/2018 |
| CN | 108066774 A | 5/2018 |
| WO | WO 99/24073 A1 | 5/1999 |
| WO | WO 2009/066955 A2 | 5/2009 |
| WO | WO 2016/149162 A1 | 9/2016 |
| WO | WO 2019/136817 A1 | 7/2019 |
| WO | WO 2020/019363 A1 | 1/2020 |

OTHER PUBLICATIONS

Joerger (Cancer Chemother Pharmacol (2016) 77:221-233) (Year: 2016).*
Chen et al. (Preparation, characterization and in vitro evaluation of solid dispersions containing Docetaxel, Drug Development and Industrial Pharmacy, 34: 588-594, 2008). (Year: 2008).*
Docetaxel product information sheet, accessed Feb. 6, 2025.*
Cabazitaxel product information sheet, accessed Feb. 6, 2025.*
International Search Report, with English Translation, for corresponding International Patent Application No. PCT/CN/2018/098227, mailed Apr. 28, 2019 (4 pages).
U.S. Advisory action, dated Nov. 4, 2022, for cross reference U.S. Appl. No. 16/652,356, (3 pages).
U.S. Non-Final Office action dated Feb. 13, 2023, for cross reference U.S. Appl. No. 16/652,356, (22 pages).

(Continued)

*Primary Examiner* — Melissa S Mercier
(74) *Attorney, Agent, or Firm* — Lewis Roca Rothgerber Christie LLP

(57) ABSTRACT

A docetaxel composition for injection and a preparation method therefor. The composition comprises the following components in parts by weight: 1 part of docetaxel, 20-60 parts of cyclodextrin, 5-80 parts of a solubilizer, 10-20 parts of stabilizer 1, 0.2-30 parts of stabilizer 2, and 0.001-1.0 part of an additive. The composition does not comprise ethanol and polysorbate, and ethanol is not used in the preparation process thereof.

9 Claims, No Drawings

(56) References Cited

OTHER PUBLICATIONS

U.S. Non-Final Office action dated Feb. 28, 2022, for cross reference U.S. Appl. No. 16/652,356, (13 pages).
U.S. Final Office action dated Jul. 25, 2022, for cross reference U.S. Appl. No. 16/652,356, (19 pages).
U.S. Restriction Requirement, dated Oct. 8, 2021, for cross reference U.S. Appl. No. 16/652,356, (8 pages).
U.S. Final Office action dated Sep. 27, 2023, for cross reference U.S. Appl. No. 16/652,356, (20 pages).

* cited by examiner

DOCETAXEL COMPOSITION FOR INJECTION AND PREPARATION METHOD THEREFOR

CROSS-REFERENCE TO RELATED APPLICATION(S)

This application is a U.S. National Phase Patent Application of PCT/CN2018/098227, filed Aug. 2, 2018, which claims priority to Chinese patent application 201810838844.1, filed on Jul. 25, 2018, the entire content of each of which is hereby incorporated by reference.

TECHNICAL FIELD

The present invention relates to the field of pharmaceutical preparations. Particularly, the present invention relates to a composition for injection containing docetaxel and preparation method therefor.

BACKGROUND OF THE INVENTION

Docetaxel is a white or almost-white powder and practically insoluble in water. It is soluble in ethanol and unstable in alkaline conditions. The chemical name for docetaxel is [2aR-(2aα, 4β, 4aβ, 6β, 9α, (aR*, βS*), 11α, 12α, 12aα, 12bα)]-β-[[(1,1-dimethylethoxy)carbonyl]amino]-α-hydroxybenzene propanoic acid [12b-acetyloxy-12-benzoyloxy-2a, 3, 4, 4a, 5, 6, 9, 10, 11, 12, 12a, 12b-dodecahydro-4, 6, 11-trihydroxy-4a, 8, 13, 13-tetramethyl-5-oxo-7, 11-methano-1H-cyclodeca-[3, 4] benz [1, 2-b]oxet-9-yl] ester.

Furthermore, docetaxel has the following structural formula:

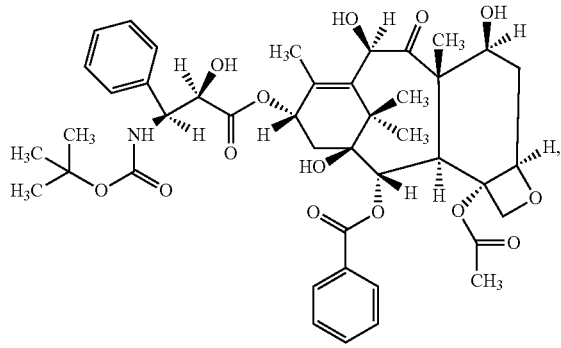

its molecular formula is: $C_{43}H_{53}NO_{14}$, and
its molecular weight is: 807.89.

Docetaxel is an antineoplastic agent of the taxanes that can be semi-synthetically prepared from precursors extracted from yew. Its anti-cancer mechanism and characteristics are similar to those of paclitaxel and belong to anti-microtubule drugs. Docetaxel inhibits the mitosis and proliferation of cancer cells through promoting the assembly of tubulin dimers into microtubules and stabilizing the microtubules by preventing the depolymerization process, and thus blocking the cancer cells at G2 and M stages. Docetaxel has a stronger pharmacological effect than paclitaxel. Specifically, compared to paclitaxel, docetaxel has an intracellular concentration of 3 times higher and a longer retention time in cells. Affinity of docetaxel to microtubules is 2 times higher than that of paclitaxel; docetaxel is twice as active as paclitaxel when serving as a microtubule stabilizer and assembly promoter; and docetaxel is twice as active as paclitaxel when serving as a microtubule-depolymerizing inhibitor. It has been shown in anti-tumor activity test in vitro that docetaxel is 1.3~12 times more active than paclitaxel. In addition, it has also been shown by clinical studies that docetaxel is more effective for anthracycline-resistant breast cancer in comparison with paclitaxel. Docetaxel is by far the most effective drug in the second-line treatment of anthracyclin-resistant breast cancer, and is also one of the most effective drugs in monotherapy and combined chemotherapy for non-small cell lung cancer.

The current formulation of docetaxel used is an injection comprising a single preparation package (containing Tween 80 and/or ethanol) and a diluent (13% ethanol in water). The earliest original product of docetaxel was a semi-synthetic anti-tumor drug developed by Sanofi-Aventis (formerly Rhone-poulenc Rorer in France), which was first marketed in Mexico, South Africa, and Canada in 1995 as a second-line treatment for advanced breast cancer and non-small cell lung cancer. In 1996, docetaxel was approved by the US FDA for the treatment of metastatic breast cancer where chemotherapy fails and metastatic non-small cell lung cancer where platinum fails. In December 2000, the combination of docetaxel and cisplatin was approved by the FDA as a first-line therapy for locally advanced or metastatic non-small cell lung cancer. At present, docetaxel has been approved for sale in nearly 100 countries and regions in the world, including China, Europe, the United States, and Japan.

Since docetaxel is lipophilic and almost insoluble in water, its original formulation TAXOTERE® employs surfactant polysorbate 80 (Tween 80, T-80) as a solubilizer and ethanol as a diluent. Packaging specification of the formulation contains two vials: (a) a TAXOTERE® injection, 20 mg docetaxel dissolved in 0.5 mL polysorbate 80; (b) a diluent, 1.5 mL 13% (w/w) ethanol solution. However, for such formulation of docetaxel, a two-step preparation process is required before administrating to patients: the first step is to mix the TAXOTERE® injection (a) with the diluent (b) to obtain a mixture with a concentration of about 10 mg/mL; the second step is to dilute the mixture obtained by the first step into a 250 mL container (non-PVC) containing either 0.9% sodium chloride solution or 5% glucose solution for injection. The concentration of docetaxel in the final infusion prepared should be 0.35 mg/mL~0.70 mg/mL, and should not exceed 0.9 mg/mL.

In the subsequent improved formulations, docetaxel, T-80 and ethanol (with or without) and other carriers are prepared into a single non-aqueous solution. However, up to now, there are no reports of docetaxel formulations containing neither T-80 nor ethanol or no literatures describing such formulations.

Polysorbate (Tween), which is a non-ionic surfactant with a peculiar smell, warm and slightly bitter, is a series of partial fatty acid esters of polyoxyethylene sorbitol. Polysorbate is widely used as an emulsifier and a solubilizer for oils. Polysorbate is generally considered to be a non-toxic and non-irritating material and is commonly used as a solubilizing carrier in injections of poorly soluble drugs. However, the injection of Tween may cause adverse effects, for example, it can cause hemolysis at low concentrations (0.01~2.0%), and further hypersensitivity reactions may be occurred during local and intramuscular injection, and in severe cases, severe hypersensitivity reactions characterized by generalized rash/erythema, hypotension and/or bronchospasm, or very rarely fatal anaphylaxis or even deaths, may been occurred. In order to reduce the adverse effects of polysorbate, premedication consisting of an antihistamine, corticosteroid and H$_2$ antagonist is needed in clinical to patients, which greatly reduces the compliance of clinical use.

The presence of polysorbate 80 in docetaxel formulation may cause severe adverse effects, and the severe adverse effects characterized by generalized rash/erythema, hypotension and/or bronchospasm, or very rarely fatal anaphylaxis, have been reported in patients. In order to reduce the adverse effects caused by polysorbate 80, an antihistamine, corticosteroid and H$_2$ antagonist is pre-administrated to patients 30 min before the administration of TAXOTERE®. Moreover, a two-step dilution is needed for TAXOTERE® before clinical use, i.e. the TAXOTERE® should be firstly diluted with a 13% (w/w) ethanol solution, and then with a 0.9% sodium chloride solution or a 5% glucose solution before administration, which not only leads to complicated steps, but also brings security risks in the use of drugs.

At the same time, in docetaxel formulations, a 13% (w/w) ethanol solution is employed as a diluent, or ethanol is employed as a co-solvent, thus adverse effects such as greater irritation, addiction and the like may be caused during the injection and administration of the docetaxel formulations due to the high concentration of ethanol therein. On 20 Jun. 2014, the U.S. Food and Drug Administration (FDA) warned that the intravenous chemotherapy drug docetaxel containing ethanol, also known as alcohol, may cause patients to experience intoxication or feel drunk during and after treatment. We are revising the labels of all docetaxel drug products to avoid this risk. Health care professionals should consider the alcohol content of docetaxel when prescribing or administering the drug to patients, particularly in those whom alcohol intake should be avoided or minimized and when using it in conjunction with other medications (www.fda.gov/Drugs/DrugSafety/ucm401752.htm#tabs-6).

It can be seen that the current docetaxel formulations per se still have great clinical risks in terms of influences of the adverse effects caused by T-80, and/or the greater irritation and the addiction caused by ethanol, and/or the risk of intoxication/drunk warned by FDA in labels of docetaxel containing ethanol. Therefore, the development of a formulation of docetaxel that contains neither T-80 nor ethanol has a very obvious clinical advantage, since it will significantly improve the safety and compliance of patients during the use of the formulation.

At the end of the 20th century, nanodrugs were derived from the combination of nanotechnology and pharmacy, that is, drugs and carriers were prepared into drug-carrying particles (such as nanoparticles, nanoliposomes, nanoemulsions) or drug nanocrystals with a particle size of 1 to 1000 nm.

Nanocrystal technology refers to that reduces the particle size of micron-sized drug particles to sub-micron level (100-1000 nm), or even nanometer level (1-100 nm) by means of physical crushing, encapsulation, broken and dispersion, precipitation crystallization or others, and by which technical problem of reducing the particle size of poorly soluble drugs to nanometer level can be solved. Nanocrystal technology can effectively improve the solubility and bioavailability of drugs due to its advantages such as reducing the particle size of the drugs, increasing the specific surface area, the saturated solubility and the membrane permeability of the drugs, and extending the retention time at absorption sites. Therefore, it provides a new solution to overcome the problem of poor oral absorption of poorly soluble drugs, and a preparation technology which is stable under the action of stabilizers.

According to the preparation method, the pharmaceutical nanocrystal technology can be classified to grinding method, crystallization method, high pressure homogenization method, emulsification method and the like. Meanwhile, the pharmaceutical nanocrystal technology also provides a novel solubilization method for poorly soluble drugs for injection. For example, the solubility of drugs in water can be increased through reducing particle size and increasing surface area of the drugs by nano-grinding; or the solubility of drugs in water can be improved by high pressure homogenization, specifically, the high pressure environment makes it easier for API to form microparticles, and homogenization can accelerate the dissolution of the drugs by accelerating the uniform dispersion of in solvents, and the combination of the two technologies can further increase the solubility of the poorly soluble drug.

Cyclodextrin, a kind of pharmaceutical carrier, has a stereo chiral interspace which is hollow and hydrophobic, and its structural characteristics of "internal hydrophobic and external hydrophilic" enable it to encapsulate a variety of small organic molecules (substrates) with suitable spatial size to form a non-covalent host-guest complex (inclusion complex). It can be seen the most significant pharmacological effect of cyclodextrin is to increase the water solubility and the stability of poorly soluble drugs.

In the prior art, some patents and/or literatures have reported cyclodextrin/docetaxel compositions without T-80: for example, patent Nos. U.S. Pat. No. 8,765,716B2/CN100411688C invented by Ren Yong et al., (pharmaceutical composition containing docetaxel-cyclodextrin inclusion complex and its preparing process) discloses a composition including docetaxel, cyclodextrin and a pharmaceutically acceptable excipient, wherein a mass ratio of docetaxel to cyclodextrin is 1:10-150. According to contents disclosed in the description and claims of this patent, ethanol is used as co-solvent in the preparation method of the composition, which is then removed under reduced pressure to form a liquid inclusion or a solid inclusion having small or trace amount of ethanol, and the content of ethanol therein is less than 1.0%. As cyclodextrin has a special interspace structure that has a certain inclusion effect on ethanol, once ethanol enters this interspace, it is impossible to completely remove it through the existing technology of reduced pressure. Furthermore, it also disclosed that "inclusion 1HNMR showed a weak ethanol methyl peak". Therefore, it can be concluded that in the composition consisting of docetaxel, cyclodextrin and a pharmaceutically acceptable excipient, the pharmaceutically acceptable excipient must be a combination of ethanol and other excipients, and the composition prepared therefrom inevitably contain small or trace amount of ethanol.

Patent Nos. CN1222321C/WO1999/024073 invented by GECZY JOSEPH M (Pharmaceutical compositions containing cyclodextrins and taxoids) discloses a composition containing taxoids and cyclodextrins, wherein the weight ratio of said taxoid to said cyclodextrin is between 1:25 and 1:250; similarly, ethanol is used as solvent in the preparation method of this composition, which is then removed under reduced pressure. In this regard, small amount of ethanol must be contained in this composition due to the structural characteristics of the cyclodextrin described above.

Patent No. US 2005/0009783 invented by Kagkadis (inclusion Complex of Taxol with 2-Hydroxypoxyproply-betacyclodextrin) discloses a composition, wherein the molar ratio of taxol and derivatives thereof to 2-hydroxypropyl-beta-cyclodextrin is 1:1000, and ethanol is also used in the preparation method.

In the patents discussed above, although T-80 is not used, ethanol is inevitably used to assist solubilization. However, there will still be some ethanol residual in the composition even it is then removed under reduced pressure, resulting that the composition can only exist in a solid form after removing the ethanol, which needs additional dilution steps before use. It can be seen a liquid form that is convenient for clinical use cannot be obtained through the above patents. Meanwhile, as disclosed in the above patents that use ethanol and cyclodextrin to solubilize taxoids, all compositions disclosed therein are prepared into a solid form by removing ethanol. Since the stable time of taxoids in an ethanol-free solution will be greatly shortened, and generally will precipitate within 24 hours, ethanol is necessary to stabilize the composition in liquid form during the reconstitution of the compositions disclosed in the above patents. For example, patent application no. WO 2016/149162 (Pharmaceutical compositions containing Taxane-cyclodextrin complexes, method of making and methods of use) invented by ZHAO William W. et al., clearly discloses that in the composition, ethanol is the one must be included and the mass ratio of ethanol to taxoids is 5:1~40:1 It can be seen even though a liquid pharmaceutical composition in which taxoids can be stable for a long time, has been prepared by this patent, the large amount of ethanol contained therein may leads to a risk of clinical medication.

In U.S. Pat. No. 6,284,746 (inclusion complexes of taxol or taxotere of *taxus* extract formed with cyclodextrins, its preparation and use) invented by Lajo Szente et al., a complex of paclitaxel or docetaxel or *Taxus brevifolia* extracts is prepared directly by using an aqueous solution or a buffer of cyclodextrin and cyclodextrin-derivative, or a solution containing a small amount of ethanol. However, the maximum solubility of API in water in the above-prepared complex does not exceed 1 mg/mL, indicating that it is difficult to prepare formulations of docetaxel that meet the clinical requirements for concentration without using ethanol or using a very small amount of ethanol.

It can be concluded after analyzing and studying the above patents that: T-80 is optional during the preparation of a stable composition of docetaxel/cyclodextrin in liquid form, but ethanol is the one must be used or present.

Given anaphylaxis caused by T-80 and adverse effects caused by ethanol in docetaxel formulations, it would be a huge innovation if a docetaxel formulation, which contains neither T-80 nor ethanol, could be prepared in a stable liquid form.

Since ethanol is used habitually in the prior art, an obvious conclusion can be obtained that without using ethanol, the cyclodextrin-containing docetaxel composition cannot be prepared into a stable liquid formulation or into a solid composition containing a small or trace amount of ethanol.

However, without being affected by the habit described above and based on a special combination formulation and a special preparation method, the inventor of the present application conducted a large number of experiments and prepared a liquid docetaxel/cyclodextrin composition which is long-term stability and a solid composition completely free of ethanol. The composition prepared by the present invention has neither T-80 nor ethanol, and no ethanol is used in the preparation method thereof.

SUMMARY OF THE INVENTION

In this regard, existing docetaxel preparations have the following defects: ethanol and/or polysorbate, which are used to dissolve or increase the solubility of docetaxel in the formulation, may lead to severe anaphylaxis, greater irritability and addiction; in addition, if docetaxel compositions are not solubilized by ethanol, a required concentration will not be reached in clinical as docetaxel has an extremely low solubility, resulting in a formulation product cannot be prepared; or the stable time of the docetaxel compositions which are not solubilized by ethanol is relatively short (generally <4 h) after diluting into solution for injection, and precipitations may be occurred during clinical use, which brings security risks in the use of the compositions.

However, the present inventors overcome the prejudice that ethanol is commonly used in the prior art to assist dissolve docetaxel, and found the liquid composition of the present invention which includes cyclodextrin and other specific co-solvents (not ethanol), stabilizers and additives, and is prepared through a method for preparing solutions commonly used in the prior art (the first method of the present invention). In addition, the inventors found that a longer preparation time was required when preparing high-concentration composition that meets the requirements for clinical use by the first method. Taking the production cost and the risk of introducing microorganisms and impurities caused by the longer preparation time into account, the inventor continued to improve the preparation method, and then developed the second method, the third method, and the fourth method.

Specifically, the inventor of the present application constitutes a solution system consisting of docetaxel, co-solvents (not ethanol), cyclodextrin, stabilizers, additives (such as citric acid, etc.) and a suitable amount of water. In said system, the solubility of docetaxel is 310 mg/mL (which can meet the general requirements for clinical use), and the maximum solubility of docetaxel can reach 40 mg/mL. Meanwhile, a GC method was used to determine whether there was ethanol in the system, and the results shown that no ethanol was detected. The solution system of the present invention can be stabilized for more than 4 h after reconstitution, indicating that it can be stored stably for a long time.

The stability of the solution system of the present invention is embodied in the following aspects: (1) samples obtained in some preferred embodiments were placed under the conditions of 25° C.±2° C. and RH 60%±5% for 24 months, and no crystal precipitation of docetaxel was observed, (2) all indicators of the samples which had been placed for 24 months under the conditions of 25° C.±2° C. and RH 60%±5%, meet the requirements of injections, and the impurity limit thereof meets the standards of USP; (3) the samples were clear and colorless during the placement, and no crystal precipitation was observed. Therefore, liquid samples of the present application can be stored stably for more than 24 months, and solid samples of the present application can be stabilized for more than 4 h after reconstitution.

In other words, the inventors of the present application overcome the prejudice of the prior art and came up with a non-obvious and even unexpected result by using a series of preparation methods: i.e found a novel composition comprising docetaxel, cyclodextrin, co-solvents (not ethanol), stabilizers and additives for injection. Furthermore, the composition found by the present inventors contains neither polysorbate nor ethanol, no ethanol is used in the preparation method thereof, although no ethanol or polysorbate is used, the present invention can still improve the characteristics of docetaxel formulations significantly.

The inventors of the present invention have found in research that by using the present composition, which comprises docetaxel, cyclodextrin, co-solvents (not ethanol), stabilizers and additives and does not comprise polysorbate and ethanol, adverse effects caused by polysorbate can be avoided and the irritation occurred during the injection of the composition and the addiction and adverse effects occurred during the administration can be reduced. Additionally, the present invention provides a docetaxel formulation whose stability has been greatly improved, i.e. provides a stable injection form without ethanol for docetaxel, and convenience for clinical use.

At the same time, the technical solutions provided by the present application have overcome the defect described in the U.S. Pat. No. 6,284,746 that, the maximum solubility of taxanes in the composition cannot reach about 1.0 mg/ml without using ethanol and polysorbate, and therefore the concentration requirement for clinical use cannot be satisfied. On the contrary, the present invention provides a method that can greatly increase the solubility of taxanes without using ethanol and polysorbate, which is not only a breakthrough but also an innovation compared with the prior art, and effectively solves the problem of clinical practicability of drugs containing taxanes.

In view of the technical problems in the prior art, the aim of the present invention is to provide a formulation of docetaxel without containing polysorbate and ethanol. The formulation of the present invention, which is in a dosage form of injection or lyophilized powder, has a property of stable quality, and can meet the requirements for clinical use and ensure the safety and effectiveness during the administration.

Technical solutions provided by the present invention are as follows.

In one aspect, the present invention provides a composition for injection containing docetaxel, the composition comprises following components in parts by weight: 1 part of docetaxel, 20-60 parts of cyclodextrin, 5-80 parts of co-solvent, 0-20 parts of stabilizer I, 0.2-30 parts of stabilizer II, 0.001-1.0 parts of additive, and the composition does not comprise ethanol and polysorbate, and no ethanol is used during its preparation.

Preferably, the composition comprises following components in parts by weight: 1 part of docetaxel, 25-50 parts of cyclodextrin, 20-70 parts of co-solvent, 0-10 parts of stabilizer I, 1-15 parts of stabilizer II, 0.001-0.5 parts of additive, and the composition does not comprise ethanol and polysorbate, and no ethanol is used during its preparation.

More preferably, the composition comprises following components in parts by weight: 1 part of docetaxel, 25-40 parts of cyclodextrin, 40-70 parts of co-solvent, 0-5 parts of stabilizer I, 4-9 parts of stabilizer II, 0.001-0.4 parts of additive, and the composition does not comprise ethanol and polysorbate, and no ethanol is used during its preparation.

Further preferably, the composition comprises following components in parts by weight: 1 part of docetaxel, 30-40 parts of cyclodextrin, 50-65 parts of co-solvent, 1-2 parts of stabilizer I, 5-8 parts of stabilizer II, 0.001-0.3 parts of additive, and the composition does not comprise ethanol and polysorbate, and no ethanol is used during its preparation.

Preferably, said cyclodextrin includes, but is not limited to, sulfobutylether-β-cyclodextrin (SBE-β-CD), hydroxypropyl-β-cyclodextrin (HP-β-CD) and/or hydroxypropyl-sulfobutylether-β-cyclodextrin (HP-SBE-β-CD); more preferably, said cyclodextrin is HP-β-CD or SBE-β-CD; further preferably, said cyclodextrin is SBE-β-CD.

Preferably, said co-solvent is one or more selected from, but not limited to, polyethylene glycol (PEG), propylene glycol and glycerol, but said co-solvent is not ethanol; more preferably, said is polyethylene glycol (PEG).

Preferably, said polyethylene glycol (PEG) is one or more selected from, but not limited to, PEG200, PEG300, PEG400, PEG600 and PEG800; more preferably, said polyethylene glycol (PEG) is PEG300 and/or PEG400.

Preferably, said stabilizer I is Poloxamer (P), more preferably, said stabilizer I is one or more selected from, but not limited to, P124, P188, P237, P338 and P407; and further preferably, said stabilizer I is P188.

Preferably, said stabilizer II is povidone (PVP), more preferably, said stabilizer II is one or more selected from, but not limited to, PVPK12, PVPK15, PVPK17, PVPK25. PVPK30 and PVPK45; and further preferably, said stabilizer II is PVPK12 and/or PVPK17.

Preferably, said additive includes, but is not limited to, citric acid and/or tartaric acid; and/or acetic acid; and/or hydrochloric acid; and/or phosphoric acid; and/or lactic acid; and/or ascorbic acid; and/or L-cysteine; and/or sodium bisulfite; and/or sodium metabisulfite; and/or edetate disodium, more preferably, said additive is citric acid.

Preferably, the composition is in a form of an aqueous solution or of a freeze-dried solid that suitable for storage.

In another aspect, the present invention provides a method for preparing the above composition for injection containing docetaxel, the method includes following steps: weighing the cyclodextrin into a container and adding the co-solvent and water thereinto, stirring the obtained system to dissolve at 20° C.-50° C., preferably 25° C., then adding the stabilizer I, the stabilizer II and the additive to the container and stirring them continuously to dissolve before adding the docetaxel to the container and filling with or without nitrogen, stirring for another 30~480 min after the docetaxel is dispersed by stirring to dissolve, finally an uniform mixture is obtained; sampling a sample from the obtained mixture to determine the pH value and content of the docetaxel in the sample and then filtering the mixture through a 0.2 μm microporous membrane after the sample is proved to be qualified, dividing the filtrate obtained into vials, filling the vials with or without nitrogen, sealing them with stoppers, and then capping and labeling the vials (the first method);

preferably, the method includes following steps:
weighing the co-solvent into a container and then adding the docetaxel thereinto, stirring the obtained system until the docetaxel is dispersed evenly into the co-solvent at 20° C.-50° C., preferably 25° C., adding cyclodextrin to the container and stirring continuously to disperse it, and then adding water thereinto and stirring the system well before adding the stabilizer I, stabilizer II and additive to the container, filling the container with or without nitrogen, stirring the system for another 30~480 min after the stabilizer I, stabilizer II and additive are dissolved by stirring, finally an uniform mixture is obtained; sampling a sample from the obtained mixture to determine the pH value and content of the docetaxel in the sample and then filtering the mixture through a 0.2 μm microporous membrane after the sample is proved to be qualified, dividing the filtrate obtained into vials, filling the vials with or without nitrogen, sealing them with stoppers, and then capping and labeling the vials (the second method);

more preferably, the method includes following steps: weighing the cyclodextrin, the co-solvent, the stabilizer I, the stabilizer II, the additive and water into a homogenizer, and at 20° C.-50° C. and 1.0 MPa~200 MPa, preferably 25° C. and 100 MPa, treating them with high-pressure homogenization for 5-30 min (10-30 cycles) to obtain an evenly dispersed and dissolved system, finally an uniform mixture is obtained after adding the docetaxel to the system and treating it with high-pressure homogenization for another 5-60 min, sampling a sample from the obtained mixture to determine the pH value and content of the docetaxel in the sample and then filtering the mixture through a 0.2 μm microporous membrane after the sample is proved to be qualified, dividing the filtrate obtained into vials, filling the vials with or without nitrogen, sealing them with stoppers, and then capping and labeling the vials (the third method);

most preferably, the method includes following steps: weighing the co-solvent into a homogenizer, adding the docetaxel thereinto, and then at 20° C.-50° C. and 1.0 MPa~200 MPa, preferably 25° C. and 100 MPa, treating them with high-pressure homogenization for 5-30 min (10-30 cycles) to enable the docetaxel to disperse and suspend or dissolve in the co-solvent, subsequently, adding the cyclodextrin, the stabilizer I, the stabilizer II, the additive and water thereinto and treating them with high-pressure homogenization for another 5-60 min. finally an uniform mixture is obtained; sampling a sample from the obtained mixture to determine the pH value and content of the docetaxel in the sample and then filtering the mixture through a 0.2 μm microporous membrane after the sample is proved to be qualified, dividing the filtrate obtained into vials, filling the vials with or without nitrogen, sealing them with stoppers, and then capping and labeling the vials (the fourth method).

The pH value of the uniform mixture obtained by the above methods (the first to the fourth method) is 3.0-6.0, preferably 4.0-5.0;

The methods described above, namely the first to the fourth methods are methods for preparing an aqueous solution intended to be stored in a form of liquid.

Further, the method of the present invention includes following steps: dividing the filtrate obtained by filtering the mixture through a 0.2 μm microporous membrane into vials, semi-sealing the vials with stoppers and then placing the vials in a freezing drier for lyophilization, then taking the vials out and filling them with or without nitrogen, sealing them with stoppers, and then capping and labeling the vails. This method is that for preparing a freeze-dried solid suitable for storage.

Through common stirring method that used in the preparation of formulations, the formulation of docetaxel of the present invention which has a good solubility and a longer stable time (after reconstitution) that satisfy clinical requirements can be prepared without using stabilizer I. T-80 and ethanol. Subsequently, the inventors further improved the preparation method and/or introduced the high-pressure homogenization method used in the nanocrystal technology, and thereby obtained a formulation of docetaxel which has a further improved solubility and can be stored stably for a long time. In addition, the production cost and the risk of introducing microorganisms and impurities caused by the longer preparation time can be avoided by using said improved preparation method or introducing the high-pressure homogenization method thereinto. Furthermore, if a certain amount of stabilizer I is introduced on the basis of the improved preparation method, the beneficial effects of the present formulation may be further amplified.

In the present invention, the co-solvent has functions of assistanting dissolution and dispersion, the cyclodextrin has a function of solubilization achieved by inclusion action and a function of stabilization, and the stabilizer can inhibit the growth of crystals of the docetaxel in the composition and stabilize the whole composition system What's more, said assistanting dissolution, dispersion, solubilization achieved by inclusion reaction, stabilization, and inhibition can work synergistically, which can be further enhanced by improving the preparation method of the composition and/or introducing the high-pressure homogenization method thereinto. Additionally, under suitable pH conditions, low concentration of metal ions, and hypoxia or near hypoxia condition formed by adding with additives for injection, the composition for injection containing docetaxel provided by the present invention can possess an excellent stability even having no polysorbate and ethanol. Specifically, the composition of the present invention has a longer stable time after reconstitution and can be stored stably for more than 24 months. Furthermore, the composition is characterized by low anaphylaxis and irritation, and will not cause adverse effects that caused by ethanol. The composition of the invention meets the standard of docetaxel for injection prescribed by USP.

The composition of the present invention has neither polysorbate nor ethanol, and can causes low histamine release, thus, the administration of an antihistamine, corticosteroid and $H_2$ antagonist is not required before administrating the composition. The present composition also has advantages of high solubility of docetaxel, high stability, longer stable time after reconstitution and convenient clinical use. Additionally, during the administration of the present composition, the risks of anaphylaxis, irritation, addiction, drunkenness and the like are significantly reduced as it contains no polysorbate and ethanol. Additionally, the present invention also provides methods for preparing the composition for injection containing docetaxel.

DETAILED DESCRIPTION OF EMBODIMENTS

The present invention will be further described in detail in combination with the specific embodiments hereinafter. It will be appreciated by those skilled in the art that the embodiments provided are only used to illustrate the present invention, rather than limiting the scope of the present invention in any way.

Stable time after reconstitution: it is an important index for investigating whether the poorly soluble drugs can be prepared to formulations that meet the requirements for clinical use. Generally, if the stable time of a diluent of the formulation is ≥4 h when being used clinically, it can be considered to meet the general requirements for clinical. In this context, the stable time after reconstitution is determined as follows, sampling a suitable amount of solution prepared in the examples according to the concentration of API in the solution, adding 5% glucose injection or normal saline thereinto in order to dilute the solution containing docetaxel to a concentration of 0.5 mg/mL that is commonly used in clinical, observing the obtained diluent with a lamp detector to determine whether there is crystallization precipitation, and recording the time when crystallization begins as the stable time.

Description for the Experimental Examples:

Since polysorbate and ethanol are not used in the present invention, it is necessary to screen the amount and type of the cyclodextrin, co-solvent, and stabilizer contained in the overall solution system. Since docetaxel is a poorly soluble drug, it is important to consider whether the docetaxel is dissolved, how much it is dissolved, and the stable time after dissolution. On the basis of that, the inventors conducted experiments on the following indicators: whether a solution can be formed, the solubility of docetaxel and stable time after reconstitution. The specific operations for determining the solubility are as follows:

weighting components (without docetaxel) according to the ratio listed in the corresponding examples and excessive docetaxel (API), preparing a supersaturated solution according to the corresponding preparation method, filtering and diluting the supersaturated solution and then determining the solubility of docetaxel in the obtained filtrate. For this part of content, see experimental examples 1-99 for details.

a) Method for Determining the Solubility:

The solubility is determined according to the standard for the determination of docetaxel for injection prescribed by USP, specifically:

High Performance Liquid Chromatography
  Solution A: water
  Solution B: acetonitrile
Mobile Phase:

| Time (min) | Solution A | Solution B |
|---|---|---|
| 0 | 72 | 28 |
| 9.0 | 72 | 28 |
| 39.0 | 28 | 72 |
| 39.1 | 0 | 100 |
| 49.0 | 0 | 100 |
| 49.1 | 72 | 28 |
| 60 | 72 | 28 |

Solvent: acetonitrile:acetic acid:water=100:0.1:100

Chromatographic Conditions
  Detector: UV232 nm
  Column: 4.6 mm×150 mm, 3.5 μm, L1
  Temperature: column temperature 45° C.
  Flow rate: 1.2 mL/min
  Injection volume: 20 μL Control Solution 0.2 mg/mL standard docetaxel. Specifically, 10 mg of standard docetaxel is taken and weighed accurately before being placed into a 50 mL flask, and then the standard docetaxel is diluted to the mark line with a solvent.

Test Solution: an appropriate amount of sample containing docetaxel is taken and weighted accurately. Then the sample is diluted with a solvent until the concentration of the docetaxel is 0.2 mg/mL.

Examples 1-11 and Experimental Examples 1-11

The first method was used in these examples and the amount of stabilizer I added was 0. Specifically: the cyclodextrin was weighted into a container and the co-solvent and water were added thereinto, the obtained system was stirred to dissolve at 20° C.-50° C. (see the table below for specific temperatures), then the stabilizer I, stabilizer II and additive were added to the container and stirred them continuously to dissolve before adding the docetaxel to the container and filling with or without nitrogen, stirred the system for another 30~480 min after the docetaxel was dispersed by stirring to dissolve, finally an uniform mixture was obtained; a sample was sampled from the obtained mixture to determine the pH value and content of the docetaxel in the sample and then filtered the mixture through a 0.2 μm microporous membrane after the sample was proved to be qualified, then the filtrate obtained was divided into vials, and the vials were then filled with or without nitrogen, sealed with stoppers, capped and labeled;

| Example | API (g) | Cyclodextrin (g) SBE-β-CD | co-solvent (g) PEG300 | Stabilizer I (g) P188 | Stabilizer II (g) PVPK12 | Additive (g) citric acid | Water |
|---|---|---|---|---|---|---|---|
| Example 1 | 0.2 | 4.0 | 1.0 | 0 | 0.04 | 0.0002 | Supplementing water until the solution has a density of 1.05~1.45 g/mL |
| Example 2 | 0.2 | 4.0 | 16.0 | 0 | 0.04 | 0.0002 | |
| Example 3 | 0.2 | 4.0 | 16.0 | 0 | 6.0 | 0.0002 | |
| Example 4 | 0.2 | 12.0 | 16.0 | 0 | 6.0 | 0.2 | |
| Example 5 | 0.2 | 12.0 | 16.0 | 0 | 3.0 | 0.1 | |
| Example 6 | 0.2 | 10.0 | 14.0 | 0 | 3.0 | 0.1 | |
| Example 7 | 0.2 | 8.0 | 12.0 | 0 | 3.0 | 0.1 | |
| Example 8 | 0.2 | 6.0 | 12.0 | 0 | 1.0 | 0.02 | |
| Example 9 | 0.2 | 7.0 | 12.0 | 0 | 1.6 | 0.002 | |
| Example 10 | 0.2 | 7.0 | 12.0 | 0 | 1.6 | 0.002 | |
| Example 11 | 0.2 | 7.0 | 12.0 | 0 | 1.6 | 0.002 | |

| Example | Temperature (° C.) | Pressure (MPa) | Stirring time (min) | Solubility of API (mg/mL) | Stable time after reconstitution (h) | Experimental example |
|---|---|---|---|---|---|---|
| Example 1 | 25 | NA | 480 | 5.56 | 4 | Experimental example 1 |
| Example 2 | 25 | NA | 480 | 5.73 | 4 | Experimental example 2 |
| Example 3 | 25 | NA | 480 | 5.76 | 48 | Experimental example 3 |
| Example 4 | 25 | NA | 480 | 12.56 | 48 | Experimental example 4 |

| Example | | | | | | |
|---|---|---|---|---|---|---|
| Example 5 | 25 | NA | 480 | 12.55 | 36 | Experimental example 5 |
| Example 6 | 25 | NA | 480 | 12.36 | 36 | Experimental example 6 |
| Example 7 | 25 | NA | 480 | 12.15 | 36 | Experimental example 7 |
| Example 8 | 25 | NA | 480 | 10.24 | 24 | Experimental example 8 |
| Example 9 | 25 | NA | 480 | 11.38 | 24 | Experimental example 9 |
| Example 10 | 25 | NA | 240 | 10.16 | 24 | Experimental example 10 |
| Example 11 | 50 | NA | 30 | 7.15 | 24 | Experimental example 11 |

Examples 12-22 and Experimental Examples 12-22

The second method was used in these examples and the amount of stabilizer I added was 0. Specifically: the co-solvent was weighted into a container and then the docetaxel was added thereinto, the obtained system was stirred at 20° C.-50° C. (see the table below for specific temperatures) until the docetaxel was dispersed evenly into the co-solvent, subsequently, the cyclodextrin was added to the container, stirred continuously to disperse it, and then water was added and stirred well before adding the stabilizer I, stabilizer II and additive to the container and filling the container with or without nitrogen, stirred the system obtained thereby for another 30~480 min after the stabilizer I, stabilizer II and additive were dissolved by stirring, finally an uniform mixture was obtained. A sample was sampled from the obtained mixture to determine the pH value and content of the docetaxel in the sample and then filtered the mixture through a 0.2 μm microporous membrane after the sample was proved to be qualified, then the filtrate obtained was divided into vials, and the vials were then filled with or without nitrogen, sealed with stoppers, capped and labeled;

| Example | API (g) | Cyclodextrin (g) SBE-β-CD | co-solvent (g) PEG300 | Stabilizer I (g) P188 | Stabilizer II (g) PVPK12 | Additive (g) citric acid | Water |
|---|---|---|---|---|---|---|---|
| Example 12 | 0.2 | 4.0 | 1.0 | 0 | 0.04 | 0.0002 | Supplementing water until the solution has a density of 1.05~1.45 g/mL |
| Example 13 | 0.2 | 4.0 | 16.0 | 0 | 0.04 | 0.0002 | |
| Example 14 | 0.2 | 4.0 | 16.0 | 0 | 6.0 | 0.0002 | |
| Example 15 | 0.2 | 12.0 | 16.0 | 0 | 6.0 | 0.2 | |
| Example 16 | 0.2 | 12.0 | 16.0 | 0 | 3.0 | 0.1 | |
| Example 17 | 0.2 | 10.0 | 14.0 | 0 | 3.0 | 0.1 | |
| Example 18 | 0.2 | 8.0 | 12.0 | 0 | 3.0 | 0.1 | |
| Example 19 | 0.2 | 6.0 | 12.0 | 0 | 1.0 | 0.02 | |
| Example 20 | 0.2 | 7.0 | 12.0 | 0 | 1.6 | 0.002 | |
| Example 21 | 0.2 | 7.0 | 12.0 | 0 | 1.6 | 0.002 | |
| Example 22 | 0.2 | 7.0 | 12.0 | 0 | 1.6 | 0.002 | |

| Example | Temperature (° C.) | Pressure (MPa) | Stirring time (min) | Solubility of API (mg/mL) | Stable time after reconstitution (h) | Experimental example |
|---|---|---|---|---|---|---|
| Example 12 | 25 | NA | 240 | 7.68 | 4 | Experimental example 12 |
| Example 13 | 25 | NA | 240 | 7.95 | 4 | Experimental example 13 |
| Example 14 | 25 | NA | 240 | 7.88 | 48 | Experimental example 14 |
| Example 15 | 25 | NA | 240 | 15.17 | 48 | Experimental example 15 |
| Example 16 | 25 | NA | 240 | 15.29 | 36 | Experimental example 16 |
| Example 17 | 25 | NA | 240 | 15.38 | 36 | Experimental example 17 |
| Example 18 | 25 | NA | 240 | 15.66 | 36 | Experimental example 18 |
| Example 19 | 25 | NA | 240 | 14.58 | 24 | Experimental example 19 |
| Example 20 | 25 | NA | 240 | 15.05 | 24 | Experimental example 20 |
| Example 21 | 25 | NA | 480 | 15.06 | 24 | Experimental example 21 |
| Example 22 | 50 | NA | 30 | 13.15 | 24 | Experimental example 22 |

Examples 23-33 and Experimental Examples 23-33

The third method was used in these examples and the amount of stabilizer I added was 0. Specifically: the cyclodextrin, the co-solvent, the stabilizer I, the stabilizer II, the additive and water were weighted into a homogenizer, and then treated them, at 20° C.-50° C. and 1.0 MPa~200 MPa (see the table below for specific temperatures and pressures), with high-pressure homogenization for 5-30 min (10-30 cycles) to obtain an evenly dispersed and dissolved system, then the system was added with the docetaxel and treated with high-pressure homogenization for another 5-60 min, finally an uniform mixture was obtained; a sample was sampled from the obtained mixture to determine the pH value and content of the docetaxel in the sample and then filtered the mixture through a 0.2 μm microporous membrane after the sample was proved to be qualified, then the filtrate obtained was divided into vials, and the vials were filled with or without nitrogen, sealed with stoppers, capped and labeled;

| Example | API (g) | Cyclodextrin SBE-β-CD (g) | co-solvent PEG300 (g) | Stabilizer I (g) P188 | Stabilizer II (g) PVPK12 | Additive (g) citric acid | Water |
|---|---|---|---|---|---|---|---|
| Example 23 | 0.2 | 4.0 | 1.0 | 0 | 0.04 | 0.0002 | Supplementing water until the solution has a density of 1.05~1.45 g/mL |
| Example 24 | 0.2 | 4.0 | 16.0 | 0 | 0.04 | 0.0002 | |
| Example 25 | 0.2 | 4.0 | 16.0 | 0 | 6.0 | 0.0002 | |
| Example 26 | 0.2 | 12.0 | 16.0 | 0 | 6.0 | 0.2 | |
| Example 27 | 0.2 | 12.0 | 16.0 | 0 | 3.0 | 0.1 | |
| Example 28 | 0.2 | 10.0 | 14.0 | 0 | 3.0 | 0.1 | |
| Example 29 | 0.2 | 8.0 | 12.0 | 0 | 3.0 | 0.1 | |
| Example 30 | 0.2 | 6.0 | 12.0 | 0 | 1.0 | 0.02 | |
| Example 31 | 0.2 | 7.0 | 12.0 | 0 | 1.6 | 0.002 | |
| Example 32 | 0.2 | 7.0 | 12.0 | 0 | 1.6 | 0.002 | |
| Example 33 | 0.2 | 7.0 | 12.0 | 0 | 1.6 | 0.002 | |

| Example | Temperature (° C.) | Pressure (MPa) | Stirring time (min) | Solubility of API (mg/mL) | Stable time after reconstitution (h) | Experimental example |
|---|---|---|---|---|---|---|
| Example 23 | 25 | 100 | 30 | 8.15 | 4 | Experimental example 23 |
| Example 24 | 25 | 100 | 30 | 8.26 | 4 | Experimental example 24 |
| Example 25 | 25 | 100 | 30 | 8.38 | 48 | Experimental example 25 |
| Example 26 | 25 | 100 | 30 | 17.75 | 48 | Experimental example 26 |
| Example 27 | 25 | 100 | 30 | 17.76 | 36 | Experimental Example 27 |
| Example 28 | 25 | 100 | 30 | 17.46 | 36 | Experimental example 28 |
| Example 29 | 25 | 100 | 30 | 17.32 | 36 | Experimental example 29 |
| Example 30 | 25 | 100 | 30 | 16.58 | 24 | Experimental example 30 |
| Example 31 | 25 | 100 | 30 | 17.15 | 24 | Experimental example 31 |
| Example 32 | 25 | 1 | 60 | 15.23 | 24 | Experimental example 32 |
| Example 33 | 50 | 200 | 5 | 18.96 | 24 | Experimental example 33 |

Examples 34-44 and Experimental Examples 34-44

The fourth method was used in these examples and the amount of stabilizer I added was 0. Specifically, the co-solvent was weighted into a homogenizer, docetaxel was added thereinto and then treated, at 20° C.-50° C. and 1.0 MPa~200 MPa (see the table below for specific temperatures and pressures), with high-pressure homogenization for 5-30 min (10-30 cycles) to enable the docetaxel to disperse and suspend or dissolve in the co-solvent, subsequently, the cyclodextrin, the stabilizer I, the stabilizer II, the additive and water were added to the homogenizer and treated with high-pressure homogenization for another 5-60 min, finally an uniform mixture was obtained; a sample was sampled from the obtained mixture to determine the pH value and content of the docetaxel in the sample and then filtered the mixture through a 0.2 μm microporous membrane after the sample was proved to be qualified, then the filtrate obtained was divided into vials, and the vials were filled with or without nitrogen, sealed with stoppers, capped and labeled;

| Example | API (g) | Cyclodextrin SBE-β-CD (g) | co-solvent PEG300 (g) | Stabilizer I (g) P188 | Stabilizer II (g) PVPK12 | Additive (g) citric acid | Water |
|---|---|---|---|---|---|---|---|
| Example 34 | 0.2 | 4.0 | 1.0 | 0 | 0.04 | 0.0002 | Supplementing water until the solution has a density of 1.05~1.45 g/mL |
| Example 35 | 0.2 | 4.0 | 16.0 | 0 | 0.04 | 0.0002 | |
| Example 36 | 0.2 | 4.0 | 16.0 | 0 | 6.0 | 0.0002 | |
| Example 37 | 0.2 | 12.0 | 16.0 | 0 | 6.0 | 0.2 | |
| Example 38 | 0.2 | 12.0 | 16.0 | 0 | 3.0 | 0.1 | |
| Example 39 | 0.2 | 10.0 | 14.0 | 0 | 3.0 | 0.1 | |
| Example 40 | 0.2 | 8.0 | 12.0 | 0 | 3.0 | 0.1 | |
| Example 41 | 0.2 | 6.0 | 12.0 | 0 | 1.0 | 0.02 | |
| Example 42 | 0.2 | 7.0 | 12.0 | 0 | 1.6 | 0.002 | |
| Example 43 | 0.2 | 7.0 | 12.0 | 0 | 1.6 | 0.002 | |
| Example 44 | 0.2 | 7.0 | 12.0 | 0 | 1.6 | 0.002 | |

| Example | Temperature (° C.) | Pressure (MPa) | Stirring time (min) | Solubility of API (mg/mL) | Stable time after reconstitution (h) | Experimental example |
|---|---|---|---|---|---|---|
| Example 34 | 25 | 100 | 30 | 8.75 | 4 | Experimental example 34 |
| Example 35 | 25 | 100 | 30 | 8.86 | 4 | Experimental example 35 |
| Example 36 | 25 | 100 | 30 | 8.96 | 48 | Experimental example 36 |
| Example 37 | 25 | 100 | 30 | 18.16 | 48 | Experimental example 37 |
| Example 38 | 25 | 100 | 30 | 18.35 | 36 | Experimental example 38 |
| Example 39 | 25 | 100 | 30 | 18.42 | 36 | Experimental example 39 |
| Example 40 | 25 | 100 | 30 | 18.26 | 36 | Experimental example 40 |
| Example 41 | 25 | 100 | 30 | 18.16 | 24 | Experimental example 41 |
| Example 42 | 25 | 100 | 30 | 18.05 | 24 | Experimental example 42 |
| Example 43 | 25 | 1 | 60 | 16.23 | 24 | Experimental example 43 |
| Example 44 | 50 | 200 | 5 | 20.38 | 24 | Experimental example 44 |

Examples 45-55 and Experimental Examples 45-55

The first method was used in these examples and the amount of stabilizer I added was not 0. Specifically: the cyclodextrin was weighted into a container and the co-solvent and water were added thereinto, the obtained system was stirred to dissolve at 20° C.-50° C. (see the table below for specific temperatures), then the stabilizer I, stabilizer II and additive were added to the container and stirred them continuously to dissolve before adding the docetaxel to the container and filling with or without nitrogen, stirred the system for another 30~480 min after the docetaxel was dispersed by stirring to dissolve, finally an uniform mixture was obtained; a sample was sampled from the obtained mixture to determine the pH value and content of the docetaxel in the sample and then filtered the mixture by a 0.2 μm microporous membrane after the sample was proved to be qualified, then the filtrate obtained was divided into vials, and the vials were then filled with or without nitrogen, sealed with stoppers, capped and labeled;

| Example | API (g) | Cyclodextrin SBE-β-CD (g) | co-solvent PEG300 (g) | Stabilizer I (g) P188 | Stabilizer II (g) PVPK12 | Additive (g) citric acid | Water |
|---|---|---|---|---|---|---|---|
| Example45 | 0.2 | 4.0 | 1.0 | 4.0 | 0.04 | 0.0002 | Supplementing water until the solution has a density of 1.05~1.45 g/mL |
| Example46 | 0.2 | 4.0 | 16.0 | 2.0 | 0.04 | 0.0002 | |
| Example47 | 0.2 | 4.0 | 16.0 | 1.0 | 6.0 | 0.0002 | |
| Example48 | 0.2 | 12.0 | 16.0 | 1.0 | 6.0 | 0.2 | |
| Example49 | 0.2 | 12.0 | 16.0 | 1.0 | 3.0 | 0.1 | |
| Example50 | 0.2 | 10.0 | 14.0 | 0.4 | 3.0 | 0.1 | |
| Example51 | 0.2 | 8.0 | 12.0 | 0.2 | 3.0 | 0.1 | |
| Example52 | 0.2 | 6.0 | 12.0 | 0.3 | 1.0 | 0.02 | |
| Example53 | 0.2 | 7.0 | 12.0 | 0.3 | 1.6 | 0.002 | |
| Example54 | 0.2 | 7.0 | 12.0 | 0.3 | 1.6 | 0.002 | |
| Example55 | 0.2 | 7.0 | 12.0 | 0.3 | 1.6 | 0.002 | |

| Example | Temperature (° C.) | Pressure (MPa) | Stirring time (min) | Solubility of API (mg/mL) | Stable time after reconstitution (h) | Experiment |
|---|---|---|---|---|---|---|
| Example45 | 25 | NA | 480 | 7.66 | 4 | Experiment 45 |
| Example46 | 25 | NA | 480 | 7.52 | 4 | Experiment 46 |
| Example47 | 25 | NA | 480 | 7.38 | 48 | Experiment 47 |
| Example48 | 25 | NA | 480 | 15.86 | 48 | Experiment 48 |
| Example49 | 25 | NA | 480 | 15.63 | 36 | Experiment 49 |
| Example50 | 25 | NA | 480 | 15.58 | 36 | Experiment 50 |
| Example51 | 25 | NA | 480 | 15.15 | 36 | Experiment 51 |
| Example52 | 25 | NA | 480 | 14.92 | 24 | Experiment 52 |
| Example53 | 25 | NA | 480 | 15.50 | 24 | Experiment 53 |
| Example54 | 25 | NA | 240 | 14.14 | 24 | Experiment 54 |
| Example55 | 50 | NA | 30 | 12.99 | 24 | Experiment 55 |

Examples 56-66 and Experimental Examples 56-66

The second method was used in these examples and the amount of stabilizer I added was not 0. Specifically: the co-solvent was weighted into a container and then the docetaxel was added thereinto, the obtained system was stirred at 20° C.-50° C. (see the table below for specific temperatures) until the docetaxel was dispersed evenly into the co-solvent, subsequently, the cyclodextrin was added to the container, stirred continuously to disperse it, and then water was added, and stirred well before adding the stabilizer I, stabilizer II and additive to the container and filling the container with or without nitrogen, stirred the system obtained thereby for another 30~480 min after the stabilizer I, stabilizer II and additive were dissolved by stirring, finally an uniform mixture was obtained, a sample was sampled from the obtained mixture to determine the pH value and content of the docetaxel in the sample and then filtered the mixture through a 0.2 μm microporous membrane after the sample was proved to be qualified, then the filtrate obtained was divided into vials, filled the vials with or without nitrogen, sealed with stoppers, capped and labeled; a sample was sampled from the obtained mixture to determine the pH value and content of docetaxel in the sample and then filtered the mixture by a 0.2 μm microporous membrane after the sample was proved to be qualified, then the filtrate obtained was divided into vials, and the vials were then filled with or without nitrogen, sealed with stoppers, capped and labeled;

| Example | API (g) | Cyclodextrin (g) SBE-β-CD | co-solvent (g) PEG300 | Stabilizer I (g) P188 | Stabilizer II (g) PVPK12 | Additive (g) citric acid | Water |
|---|---|---|---|---|---|---|---|
| Example 56 | 0.2 | 4.0 | 1.0 | 4.0 | 0.04 | 0.0002 | Supplementing water until the solution has a density of 1.05~1.45 g/mL |
| Example 57 | 0.2 | 4.0 | 16.0 | 2.0 | 0.04 | 0.0002 | |
| Example 58 | 0.2 | 4.0 | 16.0 | 1.0 | 6.0 | 0.0002 | |
| Example 59 | 0.2 | 12.0 | 16.0 | 1.0 | 6.0 | 0.2 | |
| Example 60 | 0.2 | 12.0 | 16.0 | 1.0 | 3.0 | 0.1 | |
| Example 61 | 0.2 | 10.0 | 14.0 | 0.4 | 3.0 | 0.1 | |
| Example 62 | 0.2 | 8.0 | 12.0 | 0.2 | 3.0 | 0.1 | |
| Example 63 | 0.2 | 6.0 | 12.0 | 0.3 | 1.0 | 0.02 | |
| Example 64 | 0.2 | 7.0 | 12.0 | 0.3 | 1.6 | 0.002 | |
| Example 65 | 0.2 | 7.0 | 12.0 | 0.3 | 1.6 | 0.002 | |
| Example 66 | 0.2 | 7.0 | 12.0 | 0.3 | 1.6 | 0.002 | |

| Example | Temperature (° C.) | Pressure (MPa) | Stirring time (min) | Solubility of API (mg/mL) | Stable time after reconstitution (h) | Experimental example |
|---|---|---|---|---|---|---|
| Example 56 | 25 | NA | 240 | 8.86 | 4 | Experimental example 56 |
| Example 57 | 25 | NA | 240 | 8.75 | 4 | Experimental example 57 |
| Example 58 | 25 | NA | 240 | 8.70 | 48 | Experimental example 58 |
| Example 59 | 25 | NA | 240 | 19.12 | 48 | Experimental example 59 |
| Example 60 | 25 | NA | 240 | 19.02 | 36 | Experimental example 60 |
| Example 61 | 25 | NA | 240 | 18.84 | 36 | Experimental example 61 |
| Example 62 | 25 | NA | 240 | 18.66 | 36 | Experimental example 62 |
| Example 63 | 25 | NA | 240 | 17.86 | 24 | Experimental example 63 |
| Example 64 | 25 | NA | 240 | 18.26 | 24 | Experimental example 64 |
| Example 65 | 25 | NA | 480 | 18.32 | 24 | Experimental example 65 |
| Example 66 | 50 | NA | 30 | 15.28 | 24 | Experimental example 66 |

Examples 67-77 and Experimental Examples 67-77

The third method was used in these examples and the amount of stabilizer I added was not 0. Specifically: the cyclodextrin, the co-solvent, the stabilizer I, the stabilizer II, the additive and water were weighted into a homogenizer, and then treated them, at 20° C.-50° C. and 1.0 MPa~200 MPa (see the table below for specific temperatures and pressures), with high-pressure homogenization for 5-30 min (10-30 cycles) to obtain an evenly dispersed and dissolved system, then the system was added with the docetaxel and treated with high-pressure homogenization for another 5-60 min, finally an uniform mixture was obtained; a sample was sampled from the obtained mixture to determine the pH value and content of the docetaxel in the sample and then filtered the mixture through a 0.2 μm microporous membrane after the sample was proved to be qualified, then the filtrate obtained was divided into vials, and the vials were then filled with or without nitrogen, sealed with stoppers, capped and labeled;

| Example | API (g) | Cyclodextrin SBE-β-CD (g) | co-solvent PEG300 (g) | Stabilizer II (g) P188 | Stabilizer II (g) PVPK12 | Additive (g) citric acid | Water |
|---|---|---|---|---|---|---|---|
| Example 67 | 0.2 | 4.0 | 1.0 | 4.0 | 0.04 | 0.0002 | Supplementing water until the solution has a density of 1.05~1.45 g/mL |
| Example 68 | 0.2 | 4.0 | 16.0 | 2.0 | 0.04 | 0.0002 | |
| Example 69 | 0.2 | 4.0 | 16.0 | 1.0 | 6.0 | 0.0002 | |
| Example 70 | 0.2 | 12.0 | 16.0 | 1.0 | 6.0 | 0.2 | |
| Example 71 | 0.2 | 12.0 | 16.0 | 1.0 | 3.0 | 0.1 | |
| Example 72 | 0.2 | 10.0 | 14.0 | 0.4 | 3.0 | 0.1 | |
| Example 73 | 0.2 | 8.0 | 12.0 | 0.2 | 3.0 | 0.1 | |
| Example 74 | 0.2 | 6.0 | 12.0 | 0.3 | 1.0 | 0.02 | |
| Example 75 | 0.2 | 7.0 | 12.0 | 0.3 | 1.6 | 0.002 | |
| Example 76 | 0.2 | 7.0 | 12.0 | 0.3 | 1.6 | 0.002 | |
| Example 77 | 0.2 | 7.0 | 12.0 | 0.3 | 1.6 | 0.002 | |

| Example | Temperature (° C.) | Pressure (MPa) | Stirring time (min) | Solubility of API (mg/mL) | Stable time after reconstitution (h) | Experimental example |
|---|---|---|---|---|---|---|
| Example 67 | 25 | 100 | 30 | 10.69 | 4 | Experimental example 67 |
| Example 68 | 25 | 100 | 30 | 10.85 | 4 | Experimental example 68 |
| Example 69 | 25 | 100 | 30 | 10.68 | 48 | Experimental example 69 |
| Example 70 | 25 | 100 | 30 | 25.65 | 48 | Experimental example 70 |
| Example 71 | 25 | 100 | 30 | 25.48 | 36 | Experimental example 71 |
| Example 72 | 25 | 100 | 30 | 24.99 | 36 | Experimental example 72 |
| Example 73 | 25 | 100 | 30 | 24.74 | 36 | Experimental example 73 |
| Example 74 | 25 | 100 | 30 | 23.92 | 24 | Experimental example 74 |
| Example 75 | 25 | 100 | 30 | 24.13 | 24 | Experimental example 75 |
| Example 76 | 25 | 1 | 60 | 23.97 | 24 | Experimental example 76 |
| Example 77 | 50 | 200 | 5 | 28.76 | 24 | Experimental example 77 |

Examples 78-88 and Experimental Examples 78-88

The fourth method was used in these examples and the amount of stabilizer I added was not 0. Specifically, the co-solvent was weighted into a homogenizer, docetaxel was added thereinto and then treated, at 20° C.-50° C. and 1.0 MPa~200 MPa (see the table below for specific temperatures and pressures), with high-pressure homogenization for 5-30 min (10-30 cycles) to enable the docetaxel to disperse and suspend or dissolve in the co-solvent, subsequently, the cyclodextrin, the stabilizer I, the stabilizer II, the additive and water were added to the homogenizer and treated with high-pressure homogenization for another 5-60 min, finally an uniform mixture was obtained; a sample was sampled from the obtained mixture to determine the pH value and content of the docetaxel in the sample and then filtered the mixture through a 0.2 μm microporous membrane after the sample was proved to be qualified, then the filtrate obtained was divided into vials, and the vials were then filled with or without nitrogen, sealed with stoppers, capped and labeled;

| Example | API (g) | Cyclodextrin SBE-β-CD (g) | co-solvent PEG300 (g) | Stabilizer I (g) P188 | Stabilizer II (g) PVPK12 | Additive (g) citric acid | Water |
|---|---|---|---|---|---|---|---|
| Example 78 | 0.2 | 4.0 | 1.0 | 4.0 | | 0.04 | 0.0002 | Supplementing water until the solution has a density of 1.05~1.45 g/mL |
| Example 79 | 0.2 | 4.0 | 16.0 | 2.0 | 0.04 | 0.0002 | |
| Example 80 | 0.2 | 4.0 | 16.0 | 1.0 | 6.0 | 0.0002 | |
| Example 81 | 0.2 | 12.0 | 16.0 | 1.0 | 6.0 | 0.2 | |
| Example 82 | 0.2 | 12.0 | 16.0 | 1.0 | 3.0 | 0.1 | |
| Example 83 | 0.2 | 10.0 | 14.0 | 0.4 | 3.0 | 0.1 | |
| Example 84 | 0.2 | 8.0 | 12.0 | 0.2 | 3.0 | 0.1 | |
| Example 85 | 0.2 | 6.0 | 12.0 | 0.3 | 1.0 | 0.02 | |
| Example 86 | 0.2 | 7.0 | 12.0 | 0.3 | 1.6 | 0.002 | |
| Example 87 | 0.2 | 7.0 | 12.0 | 0.3 | 1.6 | 0.002 | |
| Example 88 | 0.2 | 7.0 | 12.0 | 0.3 | 1.6 | 0.002 | |

| Example | Temperature (° C.) | Pressure (MPa) | Stirring time (min) | Solubility of API (mg/mL) | Stable time after reconstitution (h) | Experimental example |
|---|---|---|---|---|---|---|
| Example 78 | 25 | 100 | 30 | 13.65 | 4 | Experimental example 78 |
| Example 79 | 25 | 100 | 30 | 13.46 | 4 | Experimental example 79 |
| Example 80 | 25 | 100 | 30 | 13.43 | 48 | Experimental example 80 |
| Example 81 | 25 | 100 | 30 | 32.68 | 48 | Experimental example 81 |
| Example 82 | 25 | 100 | 30 | 32.57 | 36 | Experimental example 82 |
| Example 83 | 25 | 100 | 30 | 32.18 | 36 | Experimental example 83 |
| Example 84 | 25 | 100 | 30 | 32.05 | 36 | Experimental example 84 |
| Example 85 | 25 | 100 | 30 | 30.15 | 24 | Experimenal example t 85 |
| Example 86 | 25 | 100 | 30 | 31.36 | 24 | Experimental example 86 |
| Example 87 | 25 | 1 | 60 | 29.77 | 24 | Experimental example 87 |
| Example 88 | 50 | 200 | 5 | 40.19 | 24 | Experimental example 88 |

Examples 89-99 and Experiments 89-99

In examples 89-99, the types of the co-solvents, the stabilizers and the additives were screened and the fourth method was used. Specifically: the co-solvent was weighted into a homogenizer, docetaxel was added thereinto and then treated, at 20° C.-50° C. and 1.0 MPa~200 MPa (see the table below for specific temperatures and pressures), with high-pressure homogenization for 5-30 min (10-30 cycles) to enable the docetaxel to disperse and suspend or dissolve in the co-solvent, subsequently, the cyclodextrin, the stabilizer I, the stabilizer II, the additive and water were added to the homogenizer and treated with high-pressure homogenization for another 5-60 min, finally an uniform mixture was obtained; a sample was sampled from the obtained mixture to determine the pH value and content of the docetaxel in the sample and then filtered the mixture through a 0.2 μm microporous membrane after the sample was proved to be qualified, then the filtrate obtained was divided into vials, and the vials were then filled with or without nitrogen, sealed with stoppers, capped and labeled;

| Example | API (g) | Cyclodextrin (g) | co-solvent (g) | Stabilizer I (g) | Stabilizer II (g) | Additive (g) | Water |
|---|---|---|---|---|---|---|---|
| Example 89 | 0.2 | 7.0/HP-β-CD | 12.0/PEG400 | 0.3/P188 | 1.6/PVPK12 | 0.002/citric add & Sodium Bisulfite | Supplementing water until the solution has a density of 1.05~1.45 g/mL |
| Example 90 | 0.2 | 7.0/HP-SBE-β-CD | 12.0/propylene glycol | 0.3/P188 | 1.6/PVPK12 | 0.002/citric acid & Edetate DiSodium | |
| Example 91 | 0.2 | 7.0/SBE-β-CD | 12.0/PEG300 | 0.3/P407 | 1.6/PVPK12 | 0.002/citric acid | |
| Example 92 | 0.2 | 7.0/SBE-β-CD | 12.0/PEG300 | 0.3/P338 | 1.6/PVPK12 | 0.002/citric acid | |
| Example 93 | 0.2 | 7.0/SBE-β-CD | 12.0/PEG300 | 0.3/P124 | 1.6/PVPK12 | 0.002/acetic acid | |
| Example 94 | 0.2 | 7.0/SBE-β-CD | 12.0/PEG300 | 0.3/P237 | 1.6/PVPK12 | 0.002/phosphoric acid | |
| Example 95 | 0.2 | 7.0/SBE-β-CD | 12.0/glycerol | 0.3/P188 | 1.6/PVPK15 | 0.002/ascorbic acid | |
| Example 96 | 0.2 | 7.0/SBE-β-CD | 12.0/PEG600 | 0.3/P188 | 1.6/PVPK17 | 0.002/L-cysteine | |
| Example 97 | 0.2 | 7.0/SBE-β-CD | 12.0/PEG800 | 0.3/P188 | 1.6/PVPK25 | 0.002/tartaric add | |
| Example 98 | 0.2 | 7.0/SBE-β-CD | 12.0/PEG300 | 0.3/P186 | 1.6/PVPK30 | 0.002/hydrochloric acid | |
| Example 99 | 0.2 | 7.0/SBE-β-CD | 12.0/PEG300 | 0.3/P188 | 1.6/PVPK45 | 0.002/lactic acid | |

| Example | Temperature (° C.) | Pressure (MPa) | Stirring time (min) | Solubility of API (mg/mL) | Stable time after reconstitution (h) | Experiment |
|---|---|---|---|---|---|---|
| Example 89 | 25 | 100 | 30 | 30.28 | 24 | Experiment 89 |
| Example 90 | 25 | 100 | 30 | 29.65 | 24 | Experiment 90 |
| Example 91 | 25 | 100 | 30 | 30.66 | 24 | Experiment 91 |
| Example 92 | 25 | 100 | 30 | 29.44 | 24 | Experiment 92 |
| Example 93 | 25 | 1 | 30 | 28.56 | 24 | Experiment 93 |
| Example 94 | 25 | 10 | 30 | 28.32 | 24 | Experiment 94 |
| Example 95 | 25 | 100 | 30 | 28.46 | 24 | Experiment 95 |
| Example 96 | 30 | 150 | 30 | 28.47 | 24 | Experiment 96 |
| Example 97 | 40 | 100 | 30 | 26.49 | 24 | Experiment 97 |
| Example 98 | 50 | 100 | 30 | 27.15 | 24 | Experiment 98 |
| Example 99 | 25 | 100 | 30 | 30.12 | 24 | Experiment 99 |

Example 100

| | |
|---|---|
| Docetaxel | 0.2 g |
| SBE-β-CD | 7.0 g |
| PEG300 | 12.0 g |
| P188 | 0.3 g |
| PVPK12 | 1.6 g |
| Citric acid | 2 mg |
| Water | 5.0 g |

The composition of this example was prepared with the fourth method. Specifically: the co-solvent was weighted into a homogenizer, docetaxel was added thereinto and then treated, at 25° C. and 100 MPa with high-pressure homogenization for 5 min to enable the docetaxel to disperse and suspend or dissolve in the co-solvent, subsequently, the cyclodextrin, the stabilizer I, the stabilizer II, the additive and water were added to the homogenizer and treated with high-pressure homogenization for another 30 min, finally an uniform mixture was obtained; a sample was sampled from the obtained mixture to determine the pH value and content of the docetaxel in the sample and then filtered the mixture through a 0.2 μm microporous membrane after the sample was proved to be qualified, then the filtrate obtained was divided into vials, and the vials were then filled with or without nitrogen, sealed with stoppers, capped and labeled;

Stable time after reconstitution: 24 h.

In order to illustrate the inventiveness of the present invention, comparative examples and related experimental examples were performed by the inventors as follows.

Comparative Examples 1-7

The compositions of these comparative examples were prepared with the fourth method. Specifically: the co-solvent was weighted into a homogenizer, docetaxel was added thereinto and then treated, at 25° C. and 100 MPa with high-pressure homogenization for 5 min to enable the docetaxel to disperse and suspend or dissolve in the co-solvent, subsequently, the cyclodextrin, the stabilizer I, the stabilizer II, the additive and water were added to the homogenizer and treated with high-pressure homogenization for another 30 min, finally an uniform mixture was obtained; a sample was sampled from the obtained mixture to determine the pH value and content of the docetaxel in the sample and then filtered the mixture through a 0.2 μm microporous membrane after the sample was proved to be qualified, then the filtrate obtained was divided into vials, and the vials were then filled with or without nitrogen, sealed with stoppers, capped and labeled. Additionally, the stable time of the compositions prepared by these comparative examples was studied, and according to the methods described in the experimental examples, the maximum concentration of API was further determined by adding excessive API compared with that listed in these comparative examples.

Comparative Example 8

This comparative example was performed according to examples 1 and 4 disclosed in U.S. Pat. No. 8,675,716B2/CN100411688C. Specifically, 1.70 g SBE-β-CD was mixed with 5.0 ml pure water, then added dropwise slowly with a solution prepared by 100.0 mg docetaxel and 1.0 ml ethanol while stirring. After fully mixed until complete dissolution, the resulting mixture was filtered through microporous membrane of 0.2 μm. The ethanol was removed from the filtrate at 55° C. under reduced pressure. After sterilization treatment, the water was also removed under reduced pressure until dried, and then the resulting solid product was dried for 48 h under reduced pressure giving a white solid inclusion. Additionally, the stable time of the composition prepared by this comparative example was studied, and according to the methods described in the experimental examples, the maximum concentration of API was further determined by adding excessive API compared with that listed in this comparative example.

| | Comparative example | | | | | | | |
|---|---|---|---|---|---|---|---|---|
| | Comparative example 1 | Comparative example 2 | Comparative example 3 | Comparative example 4 | Comparative example 5 | Comparative example 6 | Comparative example 7 | Comparative example 8 |
| API(g) | 0.2 | 0.2 | 0.2 | 0.2 | 0.2 | 0.2 | 0.2 | 0.2 |
| SBE-β-CD(g) | 1 | 14 | 7 | 7 | 7 | 7 | 7 | 3.4 |
| PEG300(g) | 12 | 12 | 0 | 20 | 12 | 12 | 12 | NA |
| P188(g) | 0.3 | 0.3 | 0.3 | 0.3 | 6 | 0.3 | 0.3 | NA |
| PVPK12(g) | 1.6 | 1.6 | 1.6 | 1.6 | 1.6 | 0 | 8 | NA |
| citric acid(g) | 0.002 | 0.002 | 0.002 | 0.002 | 0.002 | 0.002 | 0.002 | NA |
| water (g) | | | | Suitable | | | | |
| Content of API (mg/mL) | 3.72 | 31.42 | 0.008 | 31.44 | 31.38 | 31.45 | 31.46 | 7.56 |
| Stable time after reconstitution (h) | NA | 24 | NA | 24 | 24 | 2.0 | 48 | 1.5 |
| Notes: | Suspension that cannot be clarified | | Suspension that cannot be clarified | | | | | Ethanol was used as a co-solvent, which was subsequently removed together with water |

Experimental Example 100

The content of ethanol was determined by gas chromatography as follows.

Chromatographic Conditions:

Column: InertCap 624 (Stationary Liquid: G43, Length: 60 m; ID: 0.25 mm, 1.4 μm, Shimadzu):

Detector: hydrogen flame ionization detector (FID);

Carrier gas: nitrogen;

Linear velocity: 21.5 cm/s;

Total flow: 24.0 mL/min;

Flow rate of column: 1 mL/min

Purge flow: 3.0 mL/min;

Split ratio: 20:1.

Temperature programmed conditions the initial temperature of 50° C. is kept for 5 min, then the temperature is raised to 200° C. at 10° C./min, kept for 4 min, and then sampling; total time used is 24 min.

Injection temperature: 210° C.;

FID temperature: 280° C.

Sampling size: 1 μL

Limit of detection: 5.057 ng

Limit of quantification: 1.264 ng.

The contents of ethanol in the samples prepared in examples 9, 86 and comparative example 8 were determined according to the description above. Results are summarized as follows:

| Sample | Ethanol content (mg/g) |
|---|---|
| Example 9 | not detected |
| Example 86 | not detected |
| Comparative example 8 | 1.5 |

The results show that the ethanol, which is used to improve the dissolution of docetaxel, cannot be removed completely under reduced pressure. In this regard, the composition prepared in U.S. Pat. No. 8,675,716B2/CN100411688C must contain ethanol.

Experimental Example 101

Study on the Stability of Liquid Composition:

A composition was prepared according to the method described in U.S. Pat. No. 8,675,716B2. Specifically, ethanol was added during the preparation in order to improve the dissolution of docetaxel, and then most of ethanol and water were removed under reduced pressure to obtain a solid inclusion (i.e. the composition). Further, a new liquid composition for injection containing 10 mg/mL docetaxel (compositions 1-4) was prepared using the solid inclusion and the carriers for injection used in the present invention, and then the stable time and the stable time after reconstitution of the liquid composition was studied.

Other samples were a composition for injection containing 10 mg/mL docetaxel prepared according to methods disclosed in patent application of WO2016/149162, and a composition for injection containing 10 mg/mL docetaxel prepared according to example 86 of the present invention.

Specific formulation for compositions 1-4 are as follows.

Composition 1:

| Docetaxel | 100 mg |
|---|---|
| SBE-β-CD | 3.5 g |
| Ethanol | suitable |
| Water | suitable |

Most of the ethanol and water were removed under reduced pressure, and a solid composition was obtained, and the solid was then reconstituted to a liquid composition with following substance:

| Water | 7.0 g. |
|---|---|

Composition 2:

| Docetaxel | 100 mg |
|---|---|
| SBE-β-CD | 3.5 g |
| Ethanol | suitable |
| Water | suitable |

Most of the ethanol and water were removed under reduced pressure, and a solid composition was obtained, and the solid was then reconstituted to a liquid composition with following substances:

| PEG300 | 6.0 g |
|---|---|
| citric acid | 2 mg |
| water | 2.5 g |

Composition 3:

| Docetaxel | 100 mg |
|---|---|
| SBE-β-CD | 3.5 g |
| Ethanol | suitable |
| Water | suitable |

Most of the ethanol and water were removed under reduced pressure, and a solid composition was obtained, and the solid was then reconstituted to a liquid composition with following substances:

| P188 | 150 mg |
|---|---|
| PVPK12 | 800 mg |
| citric acid | 2 mg |
| Water | 2.5 g |

Composition 4:

| Docetaxel | 100 mg |
|---|---|
| SBE-β-CD | 3.5 g |
| Ethanol | suitable |
| Water | suitable |

Most of the ethanol and water were removed under reduced pressure, and a solid composition was obtained, and the solid was then reconstituted to a liquid composition with following substances:

| | |
|---|---|
| PEG300 | 6.0 g |
| P188 | 150 mg |
| PVPK12 | 800 mg |
| Citric acid | 2 mg |
| Water | 2.5 g |

Results are summarized as follows:

| Sample | Stable time of the liquid composition (days) | Stable time after reconstitution (h) |
|---|---|---|
| Composition 1 | 1 | 2.5 |
| Composition 2 | 2 | 3.0 |
| Composition 3 | 1.5 | 2.5 |
| Composition 4 | 2 | 4.0 |
| WO 2016/149162 | >360 | 24 |
| Product of the present invention (example 86) | >360 | 24 |

It can be seen from the above results that: as ethanol, which is removed subsequently, is used during the preparation of the solid compositions in the method described in U.S. Pat. No. 8,675,716B2, the compositions 1-4 (in a form of liquid) have greatly shorted stable time (after reconstitution) even if they are obtained by reconstituting the solid compositions with the co-solvents and the stabilizers used in the present invention. This suggests that, the difference in preparation method or in types of co-solvent results in significantly difference in the stability of the composition of the present invention and that of US U.S. Pat. No. 8,675,716B2, i.e. a stable solution formulation suitable for clinical use cannot be obtained through U.S. Pat. No. 8,675,716B2. Additionally, said significantly difference may also be observed between compositions which has 99% identical components (compositions prepared according to U.S. Pat. No. 8,675,716B2 contain a small amount of ethanol) to that of the present invention, from which it can be seen even if there is only 1% difference in components (i.e. there exist a small to a trace amount of ethanol), or preparation method, the stability of the composition obtained may be significantly affected. The inventors found that there is an inherent synergy between the components of the composition of the present invention, which was unexpected prior to the experiments without ethanol, and thus the effects are unobvious. This is also confirmed by the composition prepared according to WO 2016/149162, which contains ethanol with a ratio of ethanol to API of 5:1-40:1. The composition of WO 2016/149162 can also achieve the technical effects equivalent to that of the present invention due to having more ethanol therein. However, in the clinical application, ethanol is not recommended by the FDA due to the safety problems brought by it. Therefore, from the perspective of safety for clinical use, the composition of the present invention has very obvious advantages.

Experimental Example 102

A 2000 mL sample was prepared according to the method of Example 86, and then was placed under the conditions of 25° C.±2° C. and RH 60%±5% for long-term stability investigation. The sample was tested according to USP standards as follows:
Chromatographic Conditions:
  Detection wavelength: 232 nm
  Column temperature, 45° C.
  Flow rate: 1.2 ml/min
  Sample size: 20 μL
  Solvent: acetonitrile:water=1:1
  Mobile phase A is water and mobile phase B is acetonitrile
  The elution gradient is shown in the table below.
  The HPLC gradient for detecting the content and related substances of docetaxel for injection.

| time (min) | solution A(%) | solution B(%) |
|---|---|---|
| 5 | 72 | 28 |
| 45 | 35 | 65 |
| 45.1 | 0 | 100 |
| 55 | 0 | 100 |
| 55.1 | 72 | 28 |
| 60 | 72 | 28 |

Results:

| Item | Standard Range | 0 month | 1 month | 3 months | 6 months | 9 months | 12 months | 18 months | 24 months |
|---|---|---|---|---|---|---|---|---|---|
| Properties | colorless, clear and transparent solution | qualified | qualified | qualified | qualified | qualified | qualified | qualified | qualified |
| Content | 90.0%~110.0% | 100.00 | 100.1 | 99.9 | 99.9 | 99.6 | 99.7 | 99.4 | 99.2 |
| Impurity a | 0.3% | NA | NA | NA | NA | NA | NA | NA | NA |
| Impurity b | NA | NA | NA | NA | NA | NA | NA | NA | NA |
| Impurity c | 1.3% | 0.01 | 0.01 | 0.01 | 0.02 | 0.02 | 0.03 | 0.03 | 0.03 |
| Impurity d | 1.5% | 0.03 | 0.02 | 0.03 | 0.04 | 0.05 | 0.04 | 0.05 | 0.05 |
| Impurity e | 1.0% | 0.02 | 0.03 | 0.04 | 0.08 | 0.10 | 0.11 | 0.22 | 0.28 |
| Impurity f | 0.5% | 0.02 | 0.02 | 0.02 | 0.03 | 0.03 | 0.02 | 0.02 | 0.03 |
| Single maximum impurity | 0.2% | 0.01 | 0.02 | 0.03 | 0.03 | 0.05 | 0.08 | 0.09 | 0.11 |

-continued

| Item | Standard Range | 0 month | 1 month | 3 months | 6 months | 9 months | 12 months | 18 months | 24 months |
|---|---|---|---|---|---|---|---|---|---|
| Total impurity | 3.5% | 0.21 | 0.32 | 0.35 | 0.38 | 0.43 | 0.59 | 0.89 | 0.92 |
| Stable time after reconstitution (h) | ≥4.0 | 24 | 24 | 24 | 24 | 24 | 24 | 24 | 24 |

Notes:
a: 10-deacetylbaccatin;
b: 2-debenzoyl-2-pentenoyl docetaxel
c: Crotonaldehyde analog
d: 6-oxodocetaxel
e: 4-epidocetaxel
f: 4-epid-6-oxodocetaxel.

Conclusions:

From the results of the above examples, experimental examples and comparative examples, the following conclusion can be obtained:

a), there is a synergistic effect between the cyclodextrin, the co-solvent, and the stabilizer, through which the solubility of API in the injection can be increased and the stable time after reconstitution of the present composition can be improved. The addition amounts of the stabilizer II and the cyclodextrin are positively correlated to the stable time after reconstitution, namely, the greater the addition amount is, the longer the stable time after reconstitution is. However, taking the safety and stability of these carriers themselves into account, appropriate amounts are selected by the present inventors for both carriers based on the consideration of meeting the requirements of clinical medication, and improving the safety and reducing the cost.

b). regarding the stabilizer I: the compositions prepared by the first to fourth methods can basically meet the requirements for clinical use when the addition amount of the stabilizer I is 0. However, if an appropriate amount of the stabilizer I is added, the compositions prepared with the same method and the same other components have better effects than that when the amount of the stabilizer I is 0. Furthermore, if the methods are further improved, the effect will be more obvious.

c). regarding the co-solvent: the co-solvent has a decisive influence on whether the API can be prepared to a formulation in a form of solution. In fact, the API cannot be prepared to a formulation in a form of solution if no co-solvent is added. While, the addition amount of the co-solvent is not unlimited, and it should be considered that the addition amount of the co-solvent not only can assist the dissolution of API, but also can obtain a solution in an appropriate concentration to meet the clinical requirement;

d). regarding the preparation methods: it is found during the preparation of compositions by the first to the fourth methods that, the improvement of the method can significantly increase the solubility of API in the composition, shorten the preparation time, and reduce the production cost and the risk of introducing microorganisms and impurities caused by the longer preparation time e). in view of the safety of pharmaceutical formulations, the type or amount of medical carriers should be as small as possible, and the type of the carriers should be that commonly used in prior art and meet the requirements for injection. When the amounts of cyclodextrin, co-solvent, and stabilizer are in the preferred range, the effect of the composition obtained thereby is equivalent to that of the composition obtained with cyclodextrin, co-solvent, and stabilizer which are in higher range. In other words, the effect of compositions cannot be improved significantly by further increasing the amount of the cyclodextrin, co-solvent, and stabilizer. Therefore, it is a better choice to enable the addition amount of them within the preferred range. For the selection of the additive, it is better to try to select the types of the additives that meet the safety requirements for injection and the pH requirement of formulations. Therefore, additives within the preferred range are more suitable choices.

What is claimed is:

1. A composition for injection containing docetaxel, wherein the composition comprises the following components in parts by weight: 1 part of docetaxel, 20-60 parts of cyclodextrin, 5-80 parts of co-solvent, 0-10 parts of stabilizer I, 0.2-30 parts of stabilizer II, 0.001-1.0 parts of additive;
   wherein the composition does not comprise ethanol and polysorbate, and no ethanol is used during its preparation;
   wherein the composition is in a form of an aqueous solution suitable for storage for at least 24 months without crystal precipitation;
   wherein said co-solvent is polyethylene glycol 300 (PEG300);
   wherein said stabilizer I is one or more selected from Poloxamer 124(P124), Poloxamer 188(P188), Poloxamer 237 (P237) and Poloxamer 338 (P338);
   wherein said stabilizer II is povidone K12 (PVPK12); and
   wherein said cyclodextrin is sulfobutylether-β-cyclodextrin (SBE-β-CD),
   wherein the additive is citric acid, and
   an amount of water is such that the solution has a density of 1.05 to 1.45 g/mL.

2. The composition according to claim 1, wherein the composition comprises the following components in parts by weight: 1 part of docetaxel, 25-50 parts of cyclodextrin, 20-70 parts of co-solvent, 0-10 parts of stabilizer I, 1-15 parts of stabilizer II, 0.001-0.5 parts of additive, and the composition does not comprise ethanol and polysorbate, and no ethanol is used during its preparation.

3. The composition according to claim 1, wherein the composition is prepared by one of the following methods:
   i) weighing the cyclodextrin into a container and adding the co-solvent and water thereinto, stirring the obtained system to dissolve at 20° C.-50° C., then adding the stabilizer I, the stabilizer II and the additive to the container and stirring them continuously to dissolve before adding the docetaxel to the container and filling with or without nitrogen, stirring for another 30~480 min after the docetaxel is dispersed by stirring to dissolve, finally an uniform mixture is obtained; sampling a sample from the obtained mixture to determine the pH value and content of the docetaxel in the sample and then filtering the mixture through a 0.2 μm microporous membrane after the sample is proved to be qualified, dividing the filtrate obtained into vials, filling the vials with or without nitrogen, sealing them with stoppers, and then capping and labeling the vials;

ii) weighing the co-solvent into a container and then adding the docetaxel thereinto, stirring the obtained system until the docetaxel is dispersed evenly into the co-solvent at 20° C.-50° C., adding cyclodextrin to the container and stirring continuously to disperse it, and then adding water thereinto and stirring the system well before adding the stabilizer I, stabilizer II and additive to the container, filling the container with or without nitrogen, stirring the system for another 30~480 min after the stabilizer I, stabilizer II and additive are dissolved by stirring, finally an uniform mixture is obtained; sampling a sample from the obtained mixture to determine the pH value and content of the docetaxel in the sample and then filtering the mixture through a 0.2 μm microporous membrane after the sample is proved to be qualified, dividing the filtrate obtained into vials, filling the vials with or without nitrogen, sealing them with stoppers, and then capping and labeling the vials;

iii) weighing the cyclodextrin, the co-solvent, the stabilizer I, the stabilizer II, the additive and water into a homogenizer, and at 20° C.-50° C. and 1.0 MPa~200 MPa, treating them with high-pressure homogenization for 5-30 min (10-30 cycles) to obtain an evenly dispersed and dissolved system, finally an uniform mixture is obtained after adding the docetaxel to the system and treating it with high-pressure homogenization for another 5-60 min; sampling a sample from the obtained mixture to determine the pH value and content of the docetaxel in the sample and then filtering the mixture through a 0.2 μm microporous membrane after the sample is proved to be qualified, dividing the filtrate obtained into vials, filling the vials with or without nitrogen, sealing them with stoppers, and then capping and labeling the vials; or iv) weighing the co-solvent into a homogenizer, adding the docetaxel thereinto, and then at 20° C.-50° C. and 1.0 MPa~200 MPa, treating them with high-pressure homogenization for 5-30 min (10-30 cycles) to enable the docetaxel to disperse and suspend or dissolve in the co-solvent, subsequently, adding the cyclodextrin, the stabilizer I, the stabilizer II, the additive and water thereinto and treating them with high-pressure homogenization for another 5-60 min, finally an uniform mixture is obtained; sampling a sample from the obtained mixture to determine the pH value and content of the docetaxel in the sample and then filtering the mixture through a 0.2 μm microporous membrane after the sample is proved to be qualified, dividing the filtrate obtained into vials, filling the vials with or without nitrogen, sealing them with stoppers, and then capping and labeling the vials.

4. A method for preparing the composition according to claim 1, the method is selected from one of the following methods:

i) weighing the cyclodextrin into a container and adding the co-solvent and water thereinto, stirring the obtained system to dissolve at 20° C.-50° C., then adding the stabilizer I, the stabilizer II and the additive to the container and stirring them continuously to dissolve before adding the docetaxel to the container and filling with or without nitrogen, stirring for another 30~480 min after the docetaxel is dispersed by stirring to dissolve, finally an uniform mixture is obtained; sampling a sample from the obtained mixture to determine the pH value and content of the docetaxel in the sample and then filtering the mixture through a 0.2 μm microporous membrane after the sample is proved to be qualified, dividing the filtrate obtained into vials, filling the vials with or without nitrogen, sealing them with stoppers, and then capping and labeling the vials;

ii) weighing the co-solvent into a container and then adding the docetaxel thereinto, stirring the obtained system until the docetaxel is dispersed evenly into the co-solvent at 20° C.-50° C., adding cyclodextrin to the container and stirring continuously to disperse it, and then adding water thereinto and stirring the system well before adding the stabilizer I, stabilizer II and additive to the container, filling the container with or without nitrogen, stirring the system for another 30~480 min after the stabilizer I, stabilizer II and additive are dissolved by stirring, finally an uniform mixture is obtained; sampling a sample from the obtained mixture to determine the pH value and content of the docetaxel in the sample and then filtering the mixture through a 0.2 μm microporous membrane after the sample is proved to be qualified, dividing the filtrate obtained into vials, filling the vials with or without nitrogen, sealing them with stoppers, and then capping and labeling the vials;

iii) weighing the cyclodextrin, the co-solvent, the stabilizer I, the stabilizer II, the additive and water into a homogenizer, and at 20° C.-50° C. and 1.0 MPa~200 MPa, treating them with high-pressure homogenization for 5-30 min (10-30 cycles) to obtain an evenly dispersed and dissolved system, finally an uniform mixture is obtained after adding the docetaxel to the system and treating it with high-pressure homogenization for another 5-60 min; sampling a sample from the obtained mixture to determine the pH value and content of the docetaxel in the sample and then filtering the mixture through a 0.2 μm microporous membrane after the sample is proved to be qualified, dividing the filtrate obtained into vials, filling the vials with or without nitrogen, sealing them with stoppers, and then capping and labeling the vials; or iv) weighing the co-solvent into a homogenizer, adding the docetaxel thereinto, and then at 20° C.-50° C. and 1.0 MPa~200 MPa, treating them with high-pressure homogenization for 5-30 min (10-30 cycles) to enable the docetaxel to disperse and suspend or dissolve in the co-solvent, subsequently, adding the cyclodextrin, the stabilizer I, the stabilizer II, the additive and water thereinto and treating them with high-pressure homogenization for another 5-60 min, finally an uniform mixture is obtained; sampling a sample from the obtained mixture to determine the pH value and content of the docetaxel in the sample and then filtering the mixture after the sample is proved to be qualified, dividing the filtrate obtained into vials, filling the vials with or without nitrogen, sealing them with stoppers, and then capping and labeling the vials.

5. The composition according to claim 1, wherein the composition comprises the following components in parts by weight: 1 part of docetaxel, 25-40 parts of cyclodextrin, 40-70 parts of co-solvent, 0-5 parts of stabilizer I, 4-9 parts of stabilizer II, 0.001-0.4 parts of additive, and the composition does not comprise ethanol and polysorbate, and no ethanol is used during its preparation.

6. The composition according to claim 1, wherein the composition comprises the following components in parts by weight: 1 part of docetaxel, 30-40 parts of cyclodextrin, 50-65 parts of co-solvent, 1-2 parts of stabilizer I, 5-8 parts of stabilizer II, 0.001-0.3 parts of additive, and the composition does not comprise ethanol and polysorbate, and no ethanol is used during its preparation.

7. The composition according to claim 1, wherein said stabilizer I is P188 and is comprised at 1-10 parts.

8. The composition according to claim 3, wherein the pH value of the uniform mixture is 3.0-6.0.

9. The method according to claim 4, wherein the pH value of the uniform mixture is 3.0-6.0.

\* \* \* \* \*